United States Patent [19]

Noguchi et al.

[11] Patent Number: 5,464,616
[45] Date of Patent: Nov. 7, 1995

[54] 6β-SUBSTITUTED PENICILLANIC ACIDS AS BETA-LACTAMASE INHIBITORS

[75] Inventors: Kazuharu Noguchi, Edmonton; Ronald G. Micetich, Sherwood Park; Mohsen Daneshtalab, Edmonton, all of Canada

[73] Assignee: Synphar Laboratories, Ind., Alberta, Canada

[21] Appl. No.: 285,670

[22] Filed: Aug. 4, 1994

[51] Int. Cl.[6] .................. C07D 499/76; A61K 31/425
[52] U.S. Cl. .................. 424/114; 424/400; 540/310; 514/192; 514/195
[58] Field of Search .................. 424/400, 114; 540/312, 310; 514/192, 195

[56] References Cited

U.S. PATENT DOCUMENTS

| | | | |
|---|---|---|---|
| 4,512,999 | 4/1985 | Adam-Molina et al. | 540/310 |
| 4,629,726 | 12/1986 | Vyro | 540/310 |
| 4,798,828 | 1/1989 | Osborne | 540/310 |

*Primary Examiner*—Nicholas Rizzo
*Attorney, Agent, or Firm*—Nikaido, Marmelstein, Murray & Oram

[57] ABSTRACT

A 6β-substituted penicillanic acid of the formula XII:

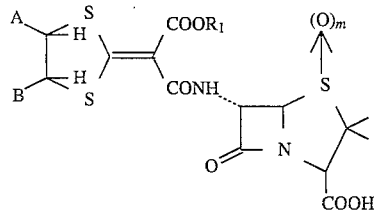

or a pharmaceutically acceptable salt or ester thereof, wherein

A and B are each hydrogen wherein the carbon atoms to which A and B are attached are linked by a single bond, or A and B together form a bond, wherein the carbon atoms to which A and B are attached are linked by a double bond, R1 is selected from the group consisting of a) hydrogen, b) a pharmaceutically acceptable salt and c) a pharmaceutically acceptable group selected from the group consisting of $C_{1-10}$ alkyl, $C_{2-10}$ alkenyl, $C_{2-10}$ alkynyl, $C_{3-10}$ cycloalkyl, $C_{3-10}$ cycloalkenyl, allyl, aryl, aralkyl, aralkenyl, aralkynyl, heterocyclyl, heterocyclylalkyl, heterocyclylalkenyl, heterocyclylalkynyl and alkylheterocyclyl; wherein said group c) is unsubstituted or substituted with a substituent selected from the group consisting of floro, chloro, bromo, iodo, azido, nitro, monoalkyl substituted amino, dialkyl substituted amino, aryl substituted amino, alkanoylamino, arylcarbonylamino, cyano, hydroxy, alkoxy, aryloxy, alkanoyloxy, arylcarbonyloxy, mercapto, alkylthio, arylthio, alkanoylthio, arylcarbonylthio, oxyimino, alkoxyimino and carboxy, and n is an integer between 0 and 2.

25 Claims, No Drawings

6β-SUBSTITUTED PENICILLANIC ACIDS AS BETA-LACTAMASE INHIBITORS

BACKGROUND OF THE INVENTION

β-Lactam antibiotics are a group of antibiotics which are used for treatment of infectious diseases caused by Gram-positive, Gram-negative, aerobic, and anaerobic bacteria. β-Lactam antibiotics are also used for the prevention of bacterial infection. Due to their high efficacy and safety, β-lactam antibiotics have been the most frequently used antimicrobial agent in many countries for the last few decades. Typical examples of clinically used β-lactam antibiotics are benzylpenicillin (penicillin G), phenoxymethylpenicillin (penicillin V), ampicillin, carbenicillin, and piperacillin, which are classified into the penicillin group; cephalothin, cephalexin, cefazolin, cephalothin, cefotaxime, ceftadizime, and ceftriaxon; which belong to the cephalosporin group; aztreonam and carmonam, which are known as monobactams; and imipenem, a member of the carbapenem class.

β-Lactamases, a group of enzymes which destroy β-lactam antibiotics by hydrolysing the β-lactam ring and make antibiotics inactive, have been known to be produced by certain bacteria from the very early stage of the history of β-lactam antibiotics as chemotherapeutic agents. After heavy usage of β-lactam antibiotics, the frequency of bacterial resistance caused by β-lactamase-production grew rapidly. The number of isolated members of β-lactamases also expanded rapidly and its number is still continuously growing.

Substances which can inhibit β-lactamases are called β-lactamase inhibitors. The effectiveness of conventional β-lactamase-susceptible β-lactam antibiotics can be enhanced by concomitant usage of such β-lactamase inhibitors. Three such inhibitors, clavulanic acid, sulbactam, and tazobactam are currently available on the market in combination with amoxycillin, ampicillin, and piperacillin, respectively (Antimicrob. Agents Chemother. 1977, 11, 852, Antimicrob. Agents Chemother. 1978, 14, 414, J. Med. Chem. 1987, 30, 1074). Although these inhibitors proved to enhance the effectiveness of conventional antibiotics against many bacteria, they failed to protect the antibiotics from one of the major classes of β-lactamases, which are known as chromosomally encoded inducible cephalosporinases or class C cephalosporinases. Due to the frequent use of the newer generation of cephalosporin antibiotics in clinics, the number of incidents of bacterial resistance caused by class C cephalosporinases is increasing. Some cephalosporin derivatives which are capable of inhibiting the cephalolsporinases are reported (Antimicrob. Agents Chemother. 1982, 21, 613).

SUMMARY OF THE INVENTION

The present invention provides novel 6β-substituted penicillanic acids of the formula I and II

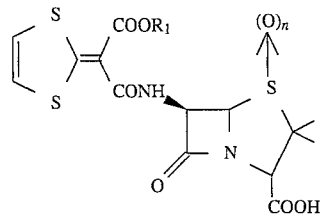

and the pharmaceutically acceptable base salts thereof and esters thereof wherein R1 is selected from hydrogen, pharmaceutically acceptable base salt, substituted or unsubstituted alkyl, alkenyl, or an alkynyl group having 1 to 10 carbon atoms, such as, for example, methyl, ethyl, propyl, isopropyl, propenyl, propynyl, butyl, isobutyl, tert.-butyl, butenyl, butynyl, pentyl, pentenyl, pentynyl, hexyl, heptyl, octyl, nonyl, decyl and the like, cycloalkyl, cycloalkenyl having 3 to 10 carbon atoms, such as, for example, cyclopropyl, cyclobutyl, cyclopentyl, cyclopentenyl, cyclohexyl, cyclohexenyl, cycloheptyl, cyclooctyl, cyclononyl, cyclodecyl, and the like, aryl group, aralkyl, aralkenyl, aralkynyl, heterocyclyl, heterocyclylalkyl, heterocyclylalkenyl, heterocyclylalkynyl, alkylheterocyclyl, in which the aryl parts of the molecule are either phenyl or naphthyl and the heterocyclic parts of the molecule contain 1 to 5 carbon atoms and at least one hetero atoms, such as, for instance, pyridinyl, pyrazinyl, pyrrolyl, furyl, thienyl, imidazolyl, triazolyl, tetrazolyl, thiazolyl, and oxazolyl, and where the substituents of the above mentioned groups may be fluoro, chloro, bromo, iodo, azido, nitro, monoalkyl or dialkyl or aryl substituted amino, alkanoylamino, arylcarbonylamino, cyano, hydroxy, alkyloxy, aryloxy, alkanoyloxy, arylcarbonyloxy, mercapto, alkylthio, arylthio, alkanoylthio, arylcarbonylthio, oxyimino, alkoxyimino, carboxy, where the substituents independent of one another occur one or more times and the alkyl parts of the molecule contain 1 to 10 carbon atoms, the alkanoyl parts of the molecule contain 1 to 6 carbon atoms, and the aryl parts of the molecule are phenyl or naphthyl; and n is an integer of 0 to 2.

Examples of the above-mentioned pharmaceutically acceptable salts are alkalimetal salt such as lithium, sodium, potassium salt or the like, alkaline earth metal salts such as calcium, magnesium salt or the like, inorganic or organic amine salts such as ammonia, ethylamine, ethanolamine, butylamine, diethylamine, morpholine, pyrrolidine, triethylamine, or the like.

Examples of the above mentioned pharmaceutically acceptable esters are easily removable groups, either chemically or enzymatically, such as, for instance, allyl, methyl, ethyl, benzyl, o-nitrobenzyl, p-nitrobenzyl, p-methoxybenzyl, diphenylmethyl, trichloroethyl, pivaloyloxymethyl, trimethysilyl, tert.-butyldimethylsilyl, triethylsilyl, or the like.

The compounds according to the invention of formula I and II and their pharmaceutically acceptable base salts are effective β-lactamase inhibitors and they protect conventional β-lactamase-susceptible β-lactam antibiotics from degradation by β-lactamases produced by bacteria. At high concentration, the compounds according to the invention inhibit a wide range of β-lactamases, whereas at low concentration, the compounds inhibit class C cephalosporinases selectively.

Accordingly, the present invention also provides an improved method for the treatment of bacterial infections caused by β-lactamase-producing bacteria in mammalian subjects, in which the compounds according to the invention are combined with conventional β-lactam antibiotics. Conventional β-lactam antibiotics here denotes so-called classical and non-classical β-lactam antibiotics. Classical β-lactam antibiotics includes penicillins and cephalosporins, whereas non-classical β-lactam antibiotics indicates such antibiotics as monobactams, penems, and carbapenems.

The invention also relates to the pharmaceutical compositions comprising a β-lactamase inhibitor of this invention and a pharmaceutically acceptable carrier or diluent.

The present invention furthermore relates to the compounds of the formula III and IV:

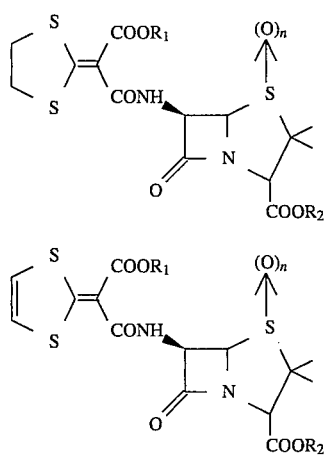

wherein $R^1$ and n are as previously defined, R2 is a carboxyl protecting group, such as, for instance, methyl, allyl, benzyl, methoxybenzyl, dimethoxybenzyl, p-nitrobenzyl, o-nitrobenzyl, benzhydryl, trichloroethyl, trimethylsilyl, triethylsilyl, triisopropylsilyl, tert-butyldimethylsilylsilyl, tert.-butyldiphenylsilyl, or pivaloyloxymethyl group. The compounds of formula of HI and IV are useful as intermediates to the β-lactamase inhibitor of the present invention of formula I and II.

The present invention also relates to 6β-substituted penicillanic acid of the formula XII:

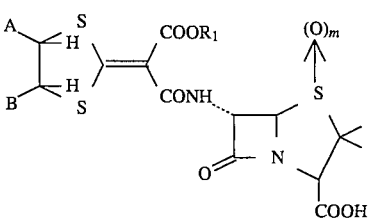

or a pharmaceutically acceptable salt or ester thereof, wherein

A and B are each hydrogen wherein the carbon atoms to which A and B are attached are linked by a single bond, or A and B together form a bond wherein the carbon atoms to which A and B are attached are linked by a double bond, R1 is selected from the group consisting of a) hydrogen, b) a pharmaceutically acceptable salt and c) a pharmaceutically acceptable group selected from the group consisting of $C_{1-10}$ alkyl, $C_{2-10}$ alkenyl, $C_{2-10}$ alkynyl, $C_{3-10}$ cycloalkyl, $C_{3-10}$ cycloalkenyl, allyl, aryl, aralkyl, aralkenyl, aralkynyl, heterocyclyl, heterocyclylalkyl, heterocyclylalkenyl, heterocyclylalkynyl and alkylheterocyclyl; wherein said group c) is unsubstituted or substituted with a substituent selected from the group consisting of floro, chloro, bromo, iodo, azido, nitro, monoalkyl substituted amino, dialkyl substituted amino, aryl substituted amino, alkanoylamino, arylcarbonylamino, cyano, hydroxy, alkoxy, aryloxy, alkanoyloxy, arylcarbonyloxy, mercapto, alkylthio, arylthio, alkanoylthio, arylcarbonylthio, oxyimino, alkoxyimino and carboxy where the substituents independent of one another occur one or more times and the alkyl parts of the molecule contain 1 to 10 carbon atoms, the alkanoyl parts of the molecule contain 1 to 6 carbon atoms, and the aryl parts of the molecule are phenyl or naphthyl; and n is an integer of 0 to 2; and n is an integer between 0 and 2.

DETAILED DESCRIPTION OF THE INVENTION

The β-lactamase inhibitors of the present invention are the compounds of formula I and II.

The compounds according to the invention are useful β-lactamase inhibitors against a wide range of β-lactamases produced by bacteria, however, it should be emphasized that the compounds according to the invention are especially potent inhibitors of clinically-important chromosomally-encoded cephalosporinases produced by Gram-negative bacteria.

For the classification of β-lactamases several methods are known. The above-mentioned cephalosporinases belong to the class I enzymes according to the method of Richmond and Sykes (Adv. Microb. Physiol. 1973, 9, 31), or group 1 according to the Bush's classification (Antimicrob. Agents Chemother. 1989, 33, 259, 264, and 271). Those cephalosporinases are also called "class C" enzymes according to the classification based on the amino acid sequences (Proc. Natl. Acad. Sci. U.S.A. 1981, 78, 4897).

Clinical problems caused by class C cephalosporinases are well-recognized by researchers and clinicians. The largest problem for class C cephalosporinase-producing bacteria are derived from the phenomenon called "derepression", which results in the stable hyper-production of cephalosporinases. The "derepression" occasionally occur after challenging Gram-negative bacteria with sub-fatal concentrations of β-lactam antibiotics. In derepressed mutants of Gram-negative bacteria, cephalosporinases are produced in such high quantities that even cephalosporinase-stable β-lactam antibiotics such as the third generation cephalosporins are destroyed gradually and extensively.

The representative compounds Ia (I, R1 =Me, n=0), Ib (I, R1=Et, n=0), Ic (I, R1=Na, n=0), Id (I, R1 =Et, n=2), and IIa (II, R1=Allyl, n=0) of the present invention were found to inhibit the representative cephalosporinase, which was isolated from *Enterobacter cloacae*, at the IC50 concentration of $6.1 \times 10^{-10}$M, $4.9 \times 10^{-10}$M, $9.1 \times 10^{-9}$M, $1.5 \times 10^{-7}$M, and $7.0 \times 10^{-9}$M, respectively. The same compounds Ia, Ib, Ic, and Id inhibited the TEM 2 enzyme from *E. coli* at the IC50 concentration of $1.4 \times 10^{-6}$M, $7.3 \times 10^{-6}$M, $9.8 \times 10^{-6}$M, $5.3 \times 10^{-5}$M, respectively. Because of such differences in IC50 value against different types of β-lactamases, these inhibitors are regarded as selective cephalosporinase-inhibitors at the low concentration.

Using whole cell bacteria, the compound Ia and Ic were demonstrated to possess synergistic activity against Gram-negative bacteria in combination with cephalothin as shown in Table 1, while the compounds Ia and Ic themselves showed no antibacterial activity at the concentration up to 128 mg/ml.

TABLE 1

MIC values of cephalothin in combination with β-lactamase inhibitors Ia and Ic.

| Microbe | MIC (μg/ml) | | |
|---|---|---|---|
| | Cephalothin | Cephalothin + Ia* | Cephalothin + Ic* |
| *E. aerogenes* S95 | >256 | 8 | 4 |
| *C. freundii* S40 | 256 | 4 | 2 |

Microbroth Dilution Method, MHB; Inoculum, 5 × 10⁵ cfu/ml; Incubation, 16 h/35° C.;
*Concentration of inhibitor = 5 mg/ml (fixed).

The compounds according to the invention are not only useful for therapeutic purposes, but also provide a useful means to study bacterial β-lactamases due to their above-mentioned high selectivity against the cephalosporinases. These inhibitors are extremely useful, for instance, as an experimental tool in such situations that the bacteria produce one of the cephalosporinases and another or more of β-lactamases from the other classes simultaneously. By adding an appropriate concentration of the inhibitors to the mixture of β-lactamases, for instance, the enzymatic effect of the cephalosporinases is selectively eliminated from the mixture and the nature of the co-existing β-lactamase(s) can be characterized more easily without isolating each enzyme.

The compounds of the present invention of formula I are prepared by the procedures depicted in the following reaction scheme:

and the compounds II are prepared by the procedure depicted in the following reaction scheme:

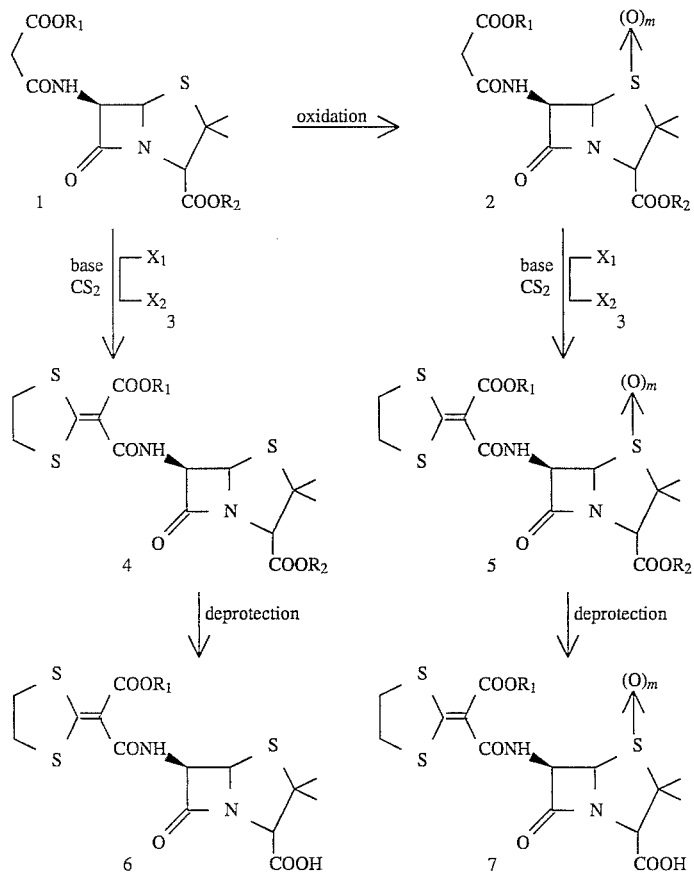

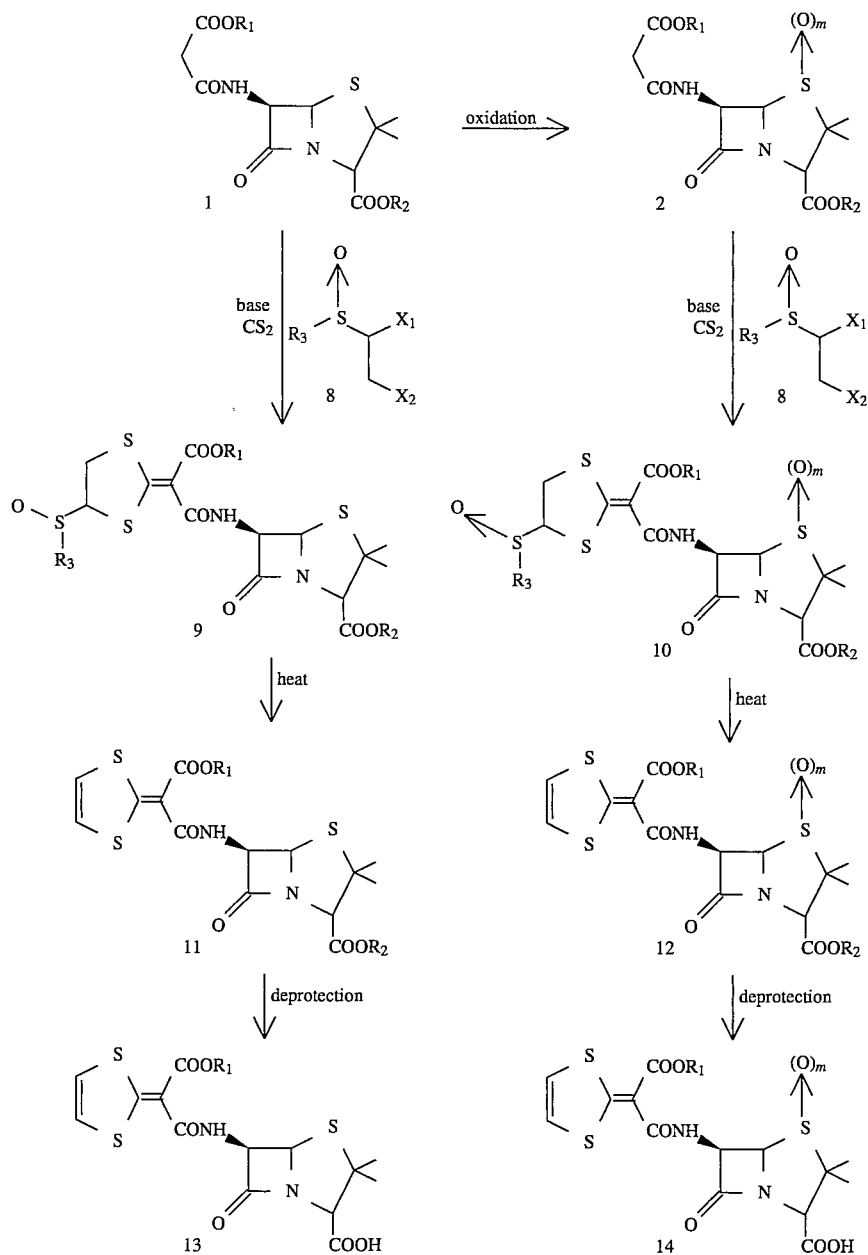

in which in both reaction schemes R 1, R2 are as defined above, m is 1 or 2, R3 is typically an unsubstituted or substituted aryl or heterocyclyl group and the like, where the substituents of the above mentioned groups may be fluoro, chloro, bromo, iodo, azido, nitro, alkyl, alkyloxy, carboxy, alkyloxycarbonyl, and the like, where the substituents independently of one another occur one or more times and the alkyl part of the molecule contain 1 to 6 carbon atoms. X1 or X2 is independent of one another selected from chloro, bromo, iodo.

The foregoing reaction diagrams are explained in greater detail as follows. Oxidation of the sulfide 1 to the sulfoxide 2 (m= 1) or sulfone 2 (m =2) can be carried out by conventional oxidizing agents. In the case of oxidation to sulfoxide 2 (m= 1), hydrogen peroxide, or peroxy-organic acid, e.g. peracetic acid, 3-chloroperoxybenzoic acid, or monoperoxyphthalic acid magnesium salt, can be used in a suitable solvent, such as, for example, dichloromethane, chloroform, carbon tetrachloride, methanol, ethanol, acetone, formic acid, acetic acid, H2O, or the like or a mixture of two or more of the above mentioned solvents. Typically, 1 to 5 equivalents of oxidizing agent is used. Oxidation to sulfoxide 2 (m= 1) can also be achieved by ozonolysis, or by treatment of 1 with general ozonides using excess oxidizing agents. The sulfone 2 (m=2) can be prepared by treating the sulfide 1 with more than 2 equivalent, typically 2 to 10 equivalents of organic peroxy acids, such as 3-chloroperoxybenzoic acid, monoperoxyphthalic acid magnesium salt or the like, in such organic solvent as dichloromethane, chloroform, carbon tetrachloride in the case of 3-chloroperoxybenzoic acid and aqueous ethanol or chloroform/H2O with phase transfer agents, or the like in the case of monoperoxyphthalic acid magnesium salt. The sulfone 2 (m=2) can also be synthesized by oxydizing the sulfide 1 by potassium permanganate in a suitable solvent, such as aqueous acetone or aqueous acetic acid. The reaction is usually carried out at the temperature between −30° C. to room temperature, and typically 2 to 5 equivalents of reagent is used. The sulfone 2 (m=2) can be derived from the sulfoxide 2 (m=1) as well using the method described for the reaction (1→2, m=2). Usually the oxidation reaction from the sulfide 1 to the sulfoxide 2 (m=1) proceeds in much milder condition than the reaction from the sulfoxide 2 (m=1) to the sulfone 2 (m=2). For instance, when 1 is oxidized to the sulfone 2 (m=2) using 3-chloroperoxybenzoic acid, the first oxidation to the sulfoxide 2 (m=1) is complete in 2 to 30 min at 0° C., whereas the next oxidation to the sulfone 2 (m=2) requires 15 to 40 h at room temperature for completion. Therefore, by choosing a suitable oxidizing agent, and by selecting a suitable reaction condition, the sulfoxide 2 (m=1) and the sulfone 2 (m=2) can be synthesized independently.

Introduction of the dithiolane group at the side chain of the sulfide 1, and the sulfoxide or sulfone 2 to form 4 and 5 can be achieved by treating 1 or 2 with 2 to 5 equivalents of a suitable base in the presence of large excess of carbon disulfide and 1 to 5 equivalents of 1,2-dihaloethane. Alternatively, carbon disulfide and 1,2-dihaloethane can be introduced after the treatment of 1 or 2 with a base. As a base, triethylamine, 1,4-diazabicyclo[2,2,2]octane (Dabco), 1,5-diazabicyclo[4,3,0]non-5-ene (DBN), 1,8-diazabicyclo[5,4,0]undec-7-ene (DBU), sodium hydride, potassium tert.-butoxide or the like can be used. The above mentioned 1,2-dihaloethane includes 1,2-dichloroethane, 1-bromo-2-chloroethane, 1-chloro-2-iodoethane, 1,2-dibromoethane, 1-bromo-2-iodoethane, 1,2-diiodoethane. The reaction is usually carried out in a suitable solvent. The preferred solvent is an aprotic solvent such as, for instance, benzene, toluene, ethylether, tetrahydrofuran, dioxane, 1,2-dimethoxyethane, dimethylformamide, 1-methyl-2-pyrrolidinone, methysulfoxide, hexamethylphosporamide, and the like. The reaction can also be done with excess carbon disulfide or excess dihaloethane without use of other solvent. In general, the reaction proceeds faster in a polar aprotic solvent such as dimethylformamide, methylsulfide or hexamethylphosporamide than in a less polar aprotic solvent. The typical reaction temperature is about −70° C. to room temperature, and the typical reaction time is about 10 min to 24 h.

Introduction of the dithiolene group at the side chain of the sulfide 1, and the sulfoxide or sulfone 2 to form 11 and 12 can be achieved by a two step reaction. First, 1 or 2 is treated with 2 to 5 equivalents of a suitable base in the presence of large excess carbon disulfide and 1 to 5 equivalent of the dihalo-reagent 8 to give the dithiolane derivative 9 and 10. Alternatively, carbon disulfide and the dihalo-reagent 8 can be introduced to the reaction mixture after 1 or 2 is treated with a base. As a base, triethylamine, 1,4-diazabicyclo[2,2,2]octane (Dabco), 1,5-diazabicyclo[4,3,0]non-5-ene (DBN), 1,8-diazabicyclo[5,4,0]undec-7-ene (DBU), sodium hydride, potasium tert.-butoxide and the like can be used. The reaction is usually carried out in a suitable solvent. The preferred solvent is an aprotic solvent such as, for instance, benzene, toluene, ethylether, tetrahydrofuran, dioxane, 1,2-dimethoxyethane, dimethylformamide, 1-methyl-2-pyrrolidinone, methylsulfoxide, hexamethylphosporamide, and the like. The reaction can also be done with excess carbon disulfide without any additional solvent. In general, the reaction proceeds faster in a polar aprotic solvent such as dimethylformamide, methylsulfide or hexamethylphosphoramide than in a less polar aprotic solvent. The typical reaction temperature is about −70° C. to room temperature, and the typical reaction time is about 10 min to 24 h. Second, 9 and 10 can be converted into 11 and 12 by heating in a suitable solvent, such as, for example, methanol, ethanol, dichloromethane, chloroform, ethyl acetate, benzene, toluene, xylene, tetrahydrofuran and the like. The typical reaction temperature is 40° C. to 150° C., and the typical reaction time is 10 min to 5 h.

The removal of the carboxyl protecting group (4→6), (5→7), (11→13), or (12→14) is carried out by conventional procedures. For example, the allyl group can be deprotected by treating the allyl ester with a 0 valent palladium catalyst such as tetrakis(triphenylphosphin)palladium (0) in the presence of 1 to 5 equivalents of an alkanoic acid alkaline salt, e.g. sodium 2-ethylhexanoate, potassium cyclohexanecarboxylate and the like, in a suitable solvent. The solvent can be a protic or aprotic solvent, such as, for example, methanol, ethanol, benzene, toluene, ethyl acetate, ethylether, tetrahydrofuran, 1,2-dimethoxyethane, dimethylformamide, methylsulfoxide and the like. Two or more of the above-mentioned solvents can be used as a mixture for the reaction. The typical amount of palladium catalyst for the reaction is 0.01 to 0.5 equivalent, and preferably 0.05 to 0.2 equivalent of catalyst is used. The typical reaction temperature for this reaction is −30° C. to room temperature, and the reaction lasts typically 5 min to 5 h. When the resulting sodium or potassium salt of the desired carboxylic acid is precipitated out from the reaction mixture, the reaction usually completes in a shorter period. The resulting sodium or potassium carboxylate can be converted to the free carboxylic acid 6 or 7 by the treatment of the carboxylate with more than 1 equivalent of organic or inorganic acids such as hydrochloric acid, sulfuric acid or the like. The substituted and unsubstituted benzyl group can be removed by catalytic hydrogenation with palladium on charcoal, palladium on alumina, and the like in a suitable solvent such as methanol, ethanol, ethyl acetate and the like with or without the presence of H2O. The typical pressure for the hydrogenation is 1 to 50 atm. The reaction completes typically within 5 min to 24 hr at room temperature. The methoxybenzyl group and the benzhydryl group can be removed by treatment of the ester with Lewis acid in the presence of anisole. As a Lewis acid, aluminum chloride or trifluoroacetic acid is typically used. 1.5 to 5 equivalent of aluminum chloride or large excess of trifluoroacetic acid is generally required. The reaction can be carried out with or without additional solvent. The preferable solvent is such aprotic solvents as dichloromethane, chloroform, benzene, toluene, ethyl ether, tetrahydrofuran, 1,2-dimethoxyethane, or the like. The typical reaction temperature is −70° C. to room temperature, and the typical reaction time is 10 min to 5 h. Removal of the trichloroethyl group can be achieved by zinc reduction in such a solvent as acetic acid, tetrahydrofuran/H2O, tetrahydrofuran/aqueous NH4Cl and the like. The typical amount of zinc is 2 to 10 equivalent, the typical reaction temperature is 0° C. to room temperature, and the typical reaction time is 5 min to 2 h. The silyl ester can be removed by treating the ester with the reagent containing a fluoro anion species, e.g. tetrabutylammonium fluoride, pyridinium fluoride and the like.

In the following, the synthesis of the starting material 1 is described. 1 is prepared either from 6-aminopenicillanic acid (15) as depicted in the following reaction scheme:

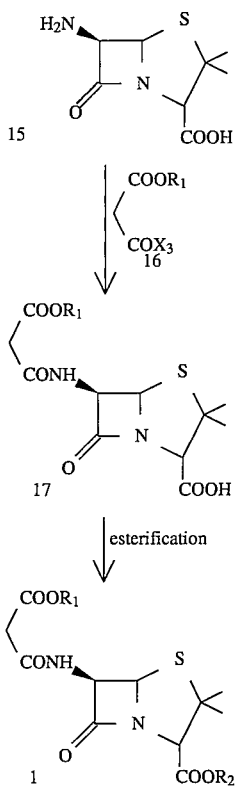

or starting from the carboxy protected 6-aminopenicillanic acid 18 as shown in the following reaction scheme:

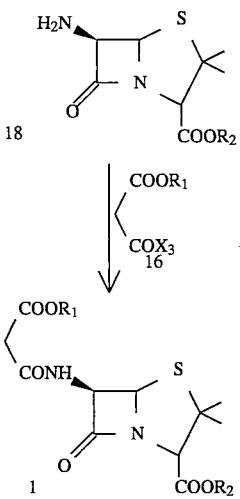

in which R1, R2 are as previously mentioned. X3 is an acyl activating group such as chloro, bromo, imidazolyl, (cyclohexyamino)(cyclohexylimino)methyloxy, benztriazolyl-N 1-oxy, phthalimide-N-oxy, and the like.

For the acylation reaction (15→17), 6-aminopenicillanic acid 15 is treated with 1 to 3 equivalents of the acylating agent 16 with or without the concomitant presence of a suitable base. Typically, 1 to 5 equivalents of base such as sodium bicarbonate, triethylamine, pyridine, 4-dimethylaminopyridine or the like is used, as required. The reaction is typically carried out in aqueous solution with or without an additional solvent. The additional solvent can be water-miscible solvent, such as acetone, methanol, ethanol, tetrahydrofuran, or non-water-miscible solvents, such as ethyl acetate, ethyl ether, benzene, toluene, dichloromethane, chloroform and the like. When the acyl chloride (X3= Cl) is used as an acylating agent, for example, a solution of the acyl chloride in an organic solvent is added to the aqueous solution of 6-aminopenicillanic acid and sodium bicarbonate for the reaction. The typical reaction temperature is 0° C. to room temperature and the typical reaction time is 10 min to 5 h.

The carboxylic acid 17 can be converted into the ester 1 by a conventional esterification reaction (general procedures can be found in Protective Groups in Organic Synthesis, T. W. Greene, A Wiley-Interscience Publication, U.S.A.). For example treating 17 in a suitable solvent, such as dichloromethane, tetrahydrofuran, dimethylformamide or methylsulfoxide, with 1 to 5 equivalents of a suitable base, such as triethylamine, sodium bicarbonate, potassium carbonate or the like, and 1 to 10 equivalents of a suitable alkyl halide, the desired esters 1 such as the allyl ester, unsubstituted or substituted benzyl esters, and others can be synthesized. Treating 17 with 1 to 2 equivalents of diphenyldiazomethane, the benzhydryl ester 1 (R2=CHPh$_2$) can be synthesized. Treating 17 with 1 to 2 equivalents of dicyclohexylcarbodiimide in the presence of excess trichloroethanol, the trichloroethyl ester 1 (R2=CH$_2$CCl$_3$) can be synthesized.

Starting from the known 6-aminopenicillanic acid esters 18 (Synthesis 1983, 549–552), 1 can be synthesized by the N-acylation reaction. Thus, treatment of 18 with 1 to 5 equivalents of the acylating agent 16 in a suitable solvent such as dichloromethane, chloroform, ethyl acetate, tetrahydrofuran, dimethylformamide, or the like, with or without a base affords the desired starting compound 1. The base can be triethylamine, pyridine, sodium bicarbonate, sodium carbonate, and the like, as required. Typically, 1 to 5 equivalents of base is used. The base can be added to the reaction mixture directly or as an aqueous solution. The typical reaction temperature is −70° C. to room temperature, and the typical reaction time is 10 min to 5 h.

The dihalo-reagent 8 is synthesized as shown in the following scheme:

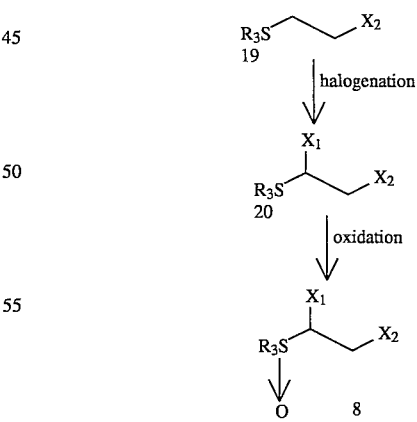

in which R3, X1, and X2 are as previously defined.

Thus, the β-halo-thioether 19 is first converted into the α,β-dihalo-thioether 20 by treating 19 with 1 to 1.5 equivalents of a suitable halogenating agent such as chlorine, sulfuryl chloride, bromine, or the like. For this reaction, an aprotic solvent which is inert to the halogenation reaction, such as dichloromethane, chloroform, carbon tetrachloride, benzene or the like, is suitably used. Typically, the reaction is carried out at −70° C. to room temperature, and the typical reaction time is 10 min to 5 h.

The oxidation reaction from the sulfide 20 to the sulfoxide 8 can be carried out by using 1 to 3 equivalent of an oxidizing agent such as hydrogen peroxide, peracetic acid, 3-chloroperoxybenzoic acid, monoperoxyphthalic acid magnesium salt or the like in a suitable solvent or a mixture of more than two solvents. Typically a solvent is selected from dichloromethane, chloroform, carbon tetrachloride, ethyl ether, ethyl acetate, $H_2O$, methanol, ethanol, formic acid, acetic acid or the like. The typical reaction time is −20° C. to 50° C., and the reaction typically takes 5 min to 2 h.

In the general description of the present invention, R1 is preferably selected from hydrogen, pharmaceutically acceptable base salts, substituted or unsubstituted alkyl, alkenyl, alkynyl group having 1 to 6 carbon atoms, cycloalkyl, cycloalkenyl having 3 to 6 carbon atoms, aryl group, aralkyl group, in which aryl parts of the molecule are either phenyl or naphthyl, and where the substituents of the above mentioned groups may be fluoro, chloro, bromo, iodo, azido, nitro, cyano, alkoxy, aryloxy, alkylthio, arylthio, alkoxyimino, carboxyl, where the substituents independent of one another occur one or more times and the alkyl parts of the molecule contain 1 to 6 carbon atoms, and the aryl parts of the molecule contain 6 to 10 carbon atoms. R2 is preferably selected from methyl, allyl, benzyl, methoxybenzyl, dimethoxybenzyl, o-nitrobenzyl, p-nitrobenzyl, benzhydrile, trichloroethyl, trimethylsilyl, triethylsilyl, triisopropylsilyl, tert.-butyldimethylsilyl, tert.-butyldiphenylsilyl, or pivaloyloxymethyl group. The preferred n is an integer of 0 to 2.

The pharmaceutically acceptable salts of compounds of formula I and II are also considered to be within the scope of this invention. These salts can be prepared by conventional procedures, for instance, by mixing the acid of formula I and II with inorganic or organic base in an aqueous, non-aqueous, or partially aqueous medium. For the salt formation, the usual basic agents are alkali metal hydride, hydroxide, alkoxide, bicarbonate, carbonate, carboxylate, alkaline earth metal hydride, hydroxide, alkoxide, and carbonate, ammonia, and organic amines. Representative examples of such base agents are, sodium hydride, sodium hydroxide, sodium methoxide, sodium bicarbonate, sodium carbonate, potassium hydroxide, potassium bicarbonate, potassium carbonate, calcium hydride, barium hydroxide, calcium carbonate, sodium 2-ethylhexanoate, ammonia, primary amines such as ethylamine, ethanolamine, butylamine, benzylamine, aniline; secondary amines such as diethylamine, morpholine, pyrrolidine, and piperidine; tertiary amines such as triethylamine, N-ethylpiperidine, 1,5-diazabicyclo[4.3.0]non-5-ene, and 1,8-diazabicyclo[5.4.0]undec-7-ene.

Preferred salts of the compounds of formula I and II are the sodium, potassium, and triethylamine salts.

As indicated hereinbefore, the compounds of formula I and II are potent β-lactamase inhibitors, and they increase the antibacterial effectiveness of the conventional β-lactam antibiotics, such as, penicillin G, penicillin V, ampicillin, amoxicillin, carbenicillin, sulbenicillin, ticarcillin, azlocillin, mezlocillin, piperacillin, aztreonam, carumonam, imipenem, meropenem, biapenem, cephalothin, cephapirin, cephalexin, cephradine, cefroxime, cefaclor, cefadroxil, cefamandole, cefazolin, cefixime, cefmetazole, cefonicid, cefoperazone, cefotaxime, cefotetane, cefoxitin, ceftizoxime, ceftriaxon, ceftazidime, cefpirome and cefepime, against many β-lactamase producing microbes. This ability of the compounds of formula I and II and their pharmaceutically acceptable salts makes these compound valuable to use concomitantly with conventional β-lactam antibiotics such as penicillins and cephalosporins to treat bacterial infections in mammals, particularly man. The compounds of formula I and II or their pharmaceutically acceptable salts can be commingled with the β-lactam antibiotic prior to treatment in order to administer two substances simultaneously, or the compounds of formula I and II or their pharmaceutically acceptable salts can be administered as a separate agent during a course of treatment with a β-lactam antibiotic. They can be administered orally, topically, or parenterally, i.e. intravenously, intramuscularly, subcutaneously, or intraperitoneally. These β-lactamase inhibitors and β-lactamase inhibitor/β-lactam antibiotic combinations can be in capsule form, tablet form, powder form, liquid solution, suspension or emulsion form, elixir form, or in ointment, cream, or lotion form.

The above mentioned preparations of the compounds according to the invention with or without a β-lactam antibiotic can contain, in addition to the active component(s), additional pharmaceutically acceptable components, such as diluents, stabilizer, antioxidants, binders, preservatives, lubricants, suspending agents, viscosity-control agents, flavors, coloring agents, or the like.

The ratio of the β-lactamase inhibitor of the invention and the β-lactam antibiotic is normally in the range of about 1:10 to 10:1, preferably, about 1:5 to 5:1. When the compounds according to the invention are used with the β-lactam antibiotic to enhance the antibacterial effectiveness of the β-lactam antibiotics, a daily dose of each active components normally range from 10 to 400 mg per kilogram of body weight for both oral and parenteral administration. However, since the dose is dependent on the state of the subject to be treated, the weight of the host, the method and frequency of administration, it may be necessary to use dosages outside the range mentioned above.

The β-lactamase inhibitor and the β-lactam antibiotic can be provided in the form of a kit. Such a kit would contain a β-lactamase inhibitor in combination with pharmaceutically acceptable carriers and a β-lactam antibiotic in combination with pharmaceutically acceptable carriers. The β-lactamase inhibitor and the β-lactam antibiotic would be separately packaged so that they can be combined before administration or administered separately.

The following examples are to further illustrate the products, processes, preparation, and treatment methods of the present invention.

EXAMPLE 1

Preparation of 6β-[(1,3-Dithiolan-2-ylidene)(methoxycarbonyl)acetamido]-2,2-dimethylpenam -3-carboxylic acid, its sodium salt and its allyl ester A. Allyl 6β-[(methoxycarbonyl)acetamido]-2,2-dimethylpenam-3-carboxylate Malonic acid monomethyl ester (2.95 g, 25 mmol) was dissolved in 25 mL of anhydrous benzene and treated with 2.5 mL of oxalyl chloride and 2 drops of dimethylformamide. The reaction mixture was stirred at room temperature for 3 h. Evaporation of the solvent gave the crude methyl malonyl chloride, which was used for the next reaction without purification.

A solution of methyl malonyl chloride (25 mmol) in 25 mL of toluene was added to a solution of 6-aminopenicillanic acid (5.41 g, 25 mmol) and sodium bicarbonate (5.25 g, 62.5 mmol) in 50 mL of $H_2O$ at 0° C. The reaction mixture was stirred at room temperature for 30 min. The aqueous layer was separated, washed with dichloromethane, and acidified with concentrated HCl solution to pH 2. The mixture was extracted with ethyl acetate several times, and the combined organic layer was washed with saturated NaCl solution. After drying over $Na_2SO_4$, the extract was concentrated in vacuo to give the crude carboxylic acid, which was subjected to the esterification reaction immediately.

The obtained carboxylic acid was dissolved in 20 mL of sieve-dried dimethylformamide, and treated with triethylamine (3.5 mL, 25 mmol) and allyl bromide (2.60 mL, 30 mmol). The reaction mixture was stirred at room temperature over night under a nitrogen atmosphere. Solvent removal gave the residue, which was taken up in dichloromethane, and washed with water and saturated NaCl solution, then dried over $Na_2SO_4$. After concentration, the residue was chromatographed on silica gel eluting with chloroform-ethyl acetate (95:5) to give the title compound (2.82 g, 32 %) as a white foam: IR ($CHCl_3$) 1790, 1740, 1685 cm$^{-1}$; $^1H$ NMR ($CDCl_3$) δ 1.51 and 1.67 (each 3H, s, $C_2$-$(CH_3)_2$), 3.30–3.45 (2H, m, $COCH_2CO$), 3.76 (3H, s, $OCH_3$), 4.48 (1H, s, $C_3$-H), 4.64–4.68 (4H, m, $OCH_2CH=CH_2$), 5.25–5.41 (4H, m, $OCH_2CH=CH_2$), 5.56 (1H, d, J=Hz, $C_5$-H), 5.75 (1H, dd, J=4 and 9Hz, $C_2$-H), 5.84–5.98 (2H, m, $OCH_2CH=CH_2$), 8.07 (1H, d, J=9Hz, NH).

B. Allyl 6β-[(1,3-dithiolan-2-ylidene)(methoxycarbonyl)acetamido]-2,2-dimethylpenam-3-carboxylate To a stirred solution of allyl 6β-[(methoxycarbonyl)acetamido]-2,2-dimethylpenam-3-carboxylate (713 mg, 2 mmol) in 2 mL of sieve-dried dimethylformamide at 0° C. was added carbon disulfide (1 mL), then sodium hydride, 60% (160 mg, 4 mmol), portionwise. The reaction mixture was stirred at 0° C. for 10 min under a nitrogen atmosphere, and treated with dibromoethane (413 mg, 2.2 mmol). The mixture was stirred at 0° C. for 30 min, diluted with toluene, washed with water and saturated NaCl solution, and dried over $Na_2SO_4$. The solution was concentrated to give a brown oil, which was chromatographed on silica gel eluting with chloroform-ethyl acetate (95:5) to yield the title compound (811 mg, 88%) as a yellow foam: IR ($CHCl_3$) 1790, 1750, 1685 cm$^{-1}$; $^1H$ NMR ($CDCl_3$) δ 1.50 and 1.67 (each 3H, s, C2-$(CH_3)_2$), 3.33 (4H, s, $SCH_2CH_2S$), 3.88 (3H, s, $CO_2CH_3$), 4.48 (1H, s, $C_3$-H), 4.64–4.68 (2H, m, $OCH_2CH=CH_2$), 5.25–5.42 (2H, m, $OCH_2CH=CH_2$), 5.58 (1H, d, J=4Hz, $C_5$-H), 5.83 (1H, dd, J=4 and 9Hz, $C_6$-H), 5.85–6.00 (1H, m, $OCH_2CH=CH_2$), 8.97 (1H, d, J=9Hz, NH).

C. Sodium 6β-[(1,3-dithiolan-2-ylidene)(methoxycarbonyl)acetamido]-2,2-dimethylpenam-3-carboxylate Allyl 6β-[(1,3-dithiolan-2-ylidene)(methoxycarbonyl)acetamido]-2,2-dimethylpenam-3-carboxylate (459 mg, 1 mmol) was dissolved in 0.25N sodium 2-ethylhexanoate/ethyl acetate solution (4 mL), and treated with triphenylphosphine (30 mg) and tetrakis(triphenylphosphine)palladium(0) (30 mg). The reaction mixture was stirred at room temperature for 2 h under a nitrogen atmosphere. The resulting precipitate was collected by filtration, washed with ethyl acetate and diethyl ether, and dried in vacuo to yield the title compound (368 mg, 84%) as a light yellow powder: $^1H$ NMR ($D_2O$) δ 1.40 and 1.50 (each 3H, s, $C_2$-$(CH3)_2$), 3.25–3.45 (4H, m, $SCH_2CH_2S$), 3.69 (3H, s, $OCH_3$), 4.13 (1H, s, $C_3$-H), 5.45–5.52 (2H, m, $C_5$-H and $C_6$).

EXAMPLE 2

Preparation of 6β-[(1,3-Dithiolan-2-ylidene)(ethoxycarbonyl)acetamido]-2,2-dimethylpenam -3-carboxylic acid, its sodium salt and its allyl ester A. Allyl 6β-[(ethoxycarbonyl)acetamido]-2,2-dimethylpenam-3-carboxylate In a manner similar to that described above for Example 1, method A, the title compound (9.35 g, 51%) was obtained from malonic acid monoethyl ester (6.61 g, 50 mmol) and 6-aminopenicillanic acid (10.8 g, 50 mmol) as colorless crystals: m.p. 68°–69° C. (toluene); IR ($CHCl_3$) 1790, 1745, 1725, 1680 cm$^{-1}$; $^1H$ NMR ($CDCl_3$) β 1.28 (3H, t, J=7Hz, $CH_2CH_3$), 1.50 and 1.67 (each 3H, s, $C_2$-$(CH_3)_2$), 3.37 (2H, s, $COCH_2CO$), 4.21 (2H, q, J=7Hz, $CH_2CH_3$), 4.48 (1H, s, $C_3$-H), 4.64–4.70 (2H, m, $OCH2CH=CH2$), 5.25–5.40 (2H, m, $OCH_2CH=CH_2$), 5.56 (1H, d, J=4Hz, $C_5$-H), 5.75 (1H, dd, J=4 and 9Hz, $C_6$-H), 5.84–6.00 (1H, m, $OCH_2CH=CH_2$), 8.11 (1H, d, J=9Hz, NH).

B. Allyl 6β-[(1,3-dithiolan-2-ylidene)(ethoxycarbonyl)acetamido]-2,2-dimethylpenam-3-carboxylate Carbon disulfide (1.5 mL), 1,2-dibromoethane (845 mg, 4.5 mmol) and sodium hydride, 60% (240 mg, 6 mmol) were added sequentially to a solution of allyl 6β-[(ethoxycarbonyl)acetamido]-2,2-dimethylpenam-3-carboxylate (1.11 g, 3 mmol) in 3 mL of dimethylformamide at 0° C. The reaction mixture was stirred at 0° C. for 30 min under a nitrogen atmosphere. The mixture was diluted with toluene, washed with water and saturated NaCl solution, and dried over $Na_2SO_4$. After concentration, the residue was chromatographed on silica gel with chloroform-ethyl acetate (95:5) as the eluant to give the title compound (926 mg, 65%) as yellow crystals: m.p. 116°–117° C. (ethyl acetate); IR ($CHCl_3$) 1790, 1750, 1680 cm$^{-1}$; $^1H$ NMR ($CDCl_3$) δ 1.39 (3H, t, J=7Hz, $CH_2CH_3$), 1.49 and 1.66 (each 3H, s, $C_2$-$(CH_3)_2$), 3.32 (4H, s, $SCH_2CH_2S$), 4.30–4.40 (2H, m, $CH_2CH_3$), 4.46 (1H, s, $C_3$-H), 4.62–4.68 (2H, m, $OCH_2CH=CH_2$), 5.26–5.40 (2H, m $OCH_2CH=CH_2$), 5.57 (1H, d, J=4Hz, $C_5$-H), 5.83 (1H, dd, J=4 and 9Hz, $C_6$-H), 5.83–6.00 (1H, m, $OCH_2CH=CH_2$), 9.05 (1H, d, J=9Hz, NH).

C. Sodium 6β-[(1,3-dithiolan-2-ylidene)(ethoxycarbonyl)acetamido]-2,2-dimethylpenam-3-carboxylate In a manner similar to that described above for Example 1, method C, the title compound (418 mg, 92%) was prepared from allyl 6β-[(1,3-dithiolan-2-ylidene)(ethoxycarbonyl)acetamido] -2,2-dimethylpenam-3-carboxylate (473 mg, 1 mmol) as a brown powder: $^1H$ NMR ($D_2O$) δ 1.21 (3H, t, J=7Hz, $CH_2CH_3$), 1.41 and 1.50 (each 3H, s, $C_2$-$(CH_3)_2$), 3.25–3.40 (4H, m, $SCH_2CH_2S$), 4.12 (1H, s, $C_3$-H), 4.10–4.20 (2H, m, $OCH_2CH_3$), 5.45–5.55 (2H, m, $C_5$-H and $C_6$-H).

D. 6β-[(1,3-Dithiolan-2-ylidene)(ethoxycarbonyl)acetamido]-2,2-dimethylpenam-3-carboxylic acid To a solution of sodium 6β-[(1,3-dithiolan-2-ylidene)(ethoxycarbonyl)acetamido]-2,2 -dimethylpenam-3-carboxylate (46 mg, 0.1 mmol) in 1 mL of $H_2O$ was added one drop (38 mg) of conc. HCl solution at 0° C. The mixture was extracted with dichloromethane several times. The combined organic layer was washed with $H_2O$ and saturated NaCl solution, dried over $Na_2SO_4$, and concentrated under reduced pressure to give the title compound (32 g, 74% yield) as a yellow oil: $^1H$ NMR ($D_2O$) δ 1.40 (3H, t, J=7Hz, $CH_2CH_3$), 1.55 and 1.66 (each 3H, s, $C_2$-$(CH_3)_2$), 3.33 (4H, s, $SCH_2CH_2S$), 4.31–4.41 (3H, m, $C_3$-H and $OCH_2CH_3$), 5.57 (1H, d, J=4Hz, C5-H), 5.82 (1H, dd, J=4 and 9Hz, C6-H), 9.03 (1H, d, J=9Hz, NH).

EXAMPLE 3

Preparation of
6β-[(1,3-Dithiolan-2-ylidene)(ethoxycarbonyl)acetamido]-2,2-dimethylpenam-3-carboxylic acid 1,1-dioxide, its sodium salt and its allyl ester A. Allyl 6β-[(ethoxycarbonyl)acetamido]-2,2-dimethylpenam-3-carboxylate 1,1-dioxide 3-Chloroperoxybenzoic acid, 80% (4.31 g, 20 mmol) was added portionwise to a cooled solution of allyl 6β-[(ethoxycarbonyl)acetamido]-2,2-dimethylpenam-3-carboxylate (3.70 g, 10 mmol) in 50 mL of anhydrous dichloromethane at 0° C. The mixture was stirred at room temperature under a nitrogen atmosphere for 16 h. After addition of 50 mL of toluene, the mixture was concentrated in vacuo to about 50 mL. The precipitated 3-chlorobenzoic acid was removed by filtration. The filtrate was washed sequentially with 10% $Na_2S_2O_3$ solution, saturated $NaHCO_3$ solution, and saturated NaCl solution, and then dried over $Na_2SO_4$. Solvent removal gave a residue, which was purified by silica gel column chromatography eluting with chloroform-ethyl acetate (90:10) to give the title compound (2.30 g, 57%) as yellow crystals: m.p. 114°–115° C. (toluene); IR ($CHCl_3$) 1815, 1755, 1730, 1690 cm$^{-1}$; $^1$H NMR ($CDCl_3$) δ 1.27 (3H, t, J=7Hz, $CH_2CH_3$), 1.40 and 1.61 (each 3H, s, $C_2$-($CH_3$)$_2$), 3.38 (2H, s, $COCH_2CO$), 4.22 (2H, q, J=7Hz, $CH_2CH_3$), 4.52 (1H, s, $C_3$-H), 4.60–4.76 (2H, m, $OCH_2CH=CH_2$), 4.78 (1H, d, J=5Hz, $C_5$-H), 5.30–5.42 (2H, m, $OCH_2CH=CH_2$), 5.84–6.00 (1H, m, $OCH_2CH=CH_2$), 6.16 (1H, dd, J=5 and 10Hz, $C_6$-H), 8.61 (1H, d, J=10Hz, NH).

B. Allyl 6β-[(1,3-dithiolan-2-ylidene)(ethoxycarbonyl)acetamido]-2,2-dimethylpenam-3-carboxylate 1,1-dioxide According to the procedure described for Example 2, method B, the title compound (535 mg, 53%) was prepared from allyl 6β-[(ethoxycarbonyl)acetamido]-2,2-dimethylpenam -3-carboxylate 1,1-dioxide (804 mg, 2 mmol) as light yellow crystals: m.p. 150°–153° C. (decomp.) (ethyl acetate); IR ($CHCl_3$) 1810, 1755, 1690 cm$^{-1}$; $^1$H NMR ($CDCl_3$) δ 1.36 (3H, t, J=7Hz, $CH_2CH_3$), 1.39 and 1.60 (each 3H, s, $C_2$-($CH_3$)$_2$), 3.33 (4H, s, $SCH_2CH_2S$), 4.30–4.43 (2H, m, $CH_2CH_3$), 4.51 (1H, s, $C_3$-H), 4.60–4.76 (2H, m, $OCH_2CH=CH_2$), 4.79 (1H, d, J=5, $C_5$-H), 5.30–5.42 (2H, m, $OCH_2CH=CH_2$), 5.85–6.00 (1H, m, $OCH_2CH=CH_2$), 6.31 (1H, dd, J=5 and 10Hz, $C_6$-H), 9.44 (1H, d, J=10Hz, NH).

C. Sodium 6β-[(1,3-dithiolan-2-ylidene)(ethoxycarbonyl)acetamido]-2,2-dimethylpenam-3-carboxylate 1,1-dioxide In a manner similar to that described above for Example 1, method C, the title compound (391 mg, 80%) was obtained from allyl 6β-[(1,3-dithiolan-2-ylidene)(ethoxycarbonyl)acetamido] -2,2-dimethylpenam-3-carboxylate 1,1-dioxide (505 mg, 1 mmol) as a brown powder: $^1$H NMR ($D_2O$) δ 1.19 (3H, t, J=7Hz, $CH_2CH_3$), 1.32 and 1.46 (each 3H, s, $C_2$-($CH_3$)$_2$), 3.25–3.40 (4H, m, $SCH_2CH_2S$), 4.10–4.25 (2H, m, $OCH_2CH_3$), 4.23 (1H, s, $C_3$-H), 5.13 (1H, d, J=4Hz, $C_5$-H), 5.99 (1H, d, J=4Hz, $C_6$-H).

EXAMPLE 4

Preparation of
6β-[(1,3-Dithiolan-2-ylidene)(carboxy)acetamido]-2,2-dimethylpenam-3-carboxylic acid, its sodium salt and its allyl ester A. Allyl 6β-[(allyloxycarbonyl)acetamido]-2,2-dimethylpenam-3-carboxylate In a manner similar to that described for Example 1, method A, the title compound (3.53 g, 46%) was prepared from malonic acid monoallyl ester (2.88 g, 20 mmol) and 6-aminopenicillanic acid (4.33 g, 20 mmol) as colorless crystals: m.p. 59°–60° C. (toluene); IR ($CHCl_3$) 1790, 1730, 1685 cm$^{-1}$; $^1$H NMR ($CDCl_3$) δ 1.51 and 1.67 (each 3H, s, $C_2$-($CH_3$)$_2$), 3.35–3.47 (2H, m, $COCH2CO$), 4.48 (1H, s, $C_3$-H), 4.60–4.70 (4H, m, 2x$OCH_2CH=CH_2$), 5.22–5.42 (4H, m, 2x$OCH_2CH=CH_2$), 5.56 (1H, d, J=4Hz, C5-H), 5.75 (1H, dd, J=4 and 9Hz, $C_6$-H), 5.84–6.00 (2H, m, 2x$OCH_2CH=CH_2$), 8.03 (1H, d, J=9Hz, NH).

B. Allyl 6β-[(allyloxycarbonyl)(1,3-dithiolan-2-ylidene)acetamido]-2,2-dimethylpenam-3-carboxylate According to the procedure described above for Example 2, method B, the title compound (843 mg, 58%) was prepared from allyl 6β-[(allyloxycarbonyl)acetamido]-2,2-dimethylpenam-3-carboxylate (1.15 g, 3 mmol) as yellow crystals: m.p. 76°–77° C. (ethyl acetate); IR ($CHCl_3$) 1790, 1750, 1680 cm$^{-1}$; $^1$H NMR ($CDCl_3$) δ 1.49 and 1.65 (each 3H, S, $C_2$-($CH_3$)$_2$), 3.33 (4H, s, $SCH_2CH_2S$), 4.46 (1H, s, $C_3$-H), 4.60–4.82 (4H, m, 2x$OCH_2CH=CH_2$), 5.24–5.44 (4H, m, 2x$OCH_2CH=CH_2$), 5.57 (1H, d, J=4, $C_5$-H), 5.82 (1H, dd, J=4 and 9Hz, $C_6$-H), 5.82–6.08 (2H, m, 2x$OCH_2CH=CH_2$), 8.99 (1H, d, J=9Hz, NH).

C. Disodium 6β-[carboxylato(1,3-dithiolan-2-ylidene)acetamido]-2,2-dimethylpenam-3-carboxylate Allyl 6β-[(allyloxycarbonyl)(1,3-dithiolan-2-ylidene)acetamido]-2,2-dimethylpenam-3-carboxylate (485 mg, 1 mmol) was dissolved in a mixture of dimethylformamide (2 mL), ethyl acetate (2 mL) and 0.5N sodium 2-ethylhexanoate/ethyl acetate solution (4 mL), and treated with triphenyl-phosphine (30 mg) and tetrakis(triphenylphosphine)palladium(0) (30 mg). The reaction mixture was stirred at room temperature for 1 h under a nitrogen atmosphere. The resulting precipitate was collected by filtration, washed successively with ethyl acetate and diethyl ether, and dried under vacuum to give the title compound (388 mg, 87%) as a light yellow powder: $^1$H NMR ($D_2O$) δ 1.31 and 1.36 (each 3H, s, $C_2$-($CH_3$)$_2$), 3.30–3.50 (4H, m, $SCH_2CH_2S$), 3.96 (1H, s, $C_3$-H), 5.98 (1H, d, J=5Hz, $C_6$-H).

EXAMPLE 5

Preparation of 6β-[(1,3-Dithiolan-2-ylidene)-(carboxy)acetamido]-2,2-dimethylpenam-3-carboxylic acid 1,1-dioxide, its sodium salt and its allyl ester A. Allyl 6β-[(allyloxycarbonyl)acetamido]-2,2-dimethylpenam-3-carboxylate 1,1-dioxide According to the procedure described above for Example 3, method A, the title compound (843 mg, 41%) was obtained from allyl 6β-[(allyloxycarbonyl)acetamido]-2,2-dimethylpenam-3-carboxylate (1.91 g, 5 mmol) as colorless crystals: m.p. 104°–106° C. (toluene); IR ($CHCl_3$) 1815, 1755, 1730, 1690 cm$^{-1}$; $^1$H NMR ($CDCl_3$) δ 1.40 and 1.61 (each 3H, s, $C_2$-($CH_3$)$_2$), 3.42 (2H, s, $COCH_2CO$), 4.52 (1H, s, $C_3$-H), 4.64–4.72 (4H, m, 2x$OCH_2CH=CH_2$), 4.78 (1H, d, J=5Hz, $C_5$-H), 5.24–5.43 (4H, m, 2x$OCH_2CH=CH_2$), 5.83–5.99 (2H, m, 2xOCH$_2$CH=CH$_2$), 6.16 (1H, dd, J=5 and 10Hz, C$_6$-H), 8.56 (1H, d, J=10Hz, NH).

B. Allyl 6β-[(allyloxycarbonyl)(1,3-dithiolan-2-ylidene)acetamido]-2,2-dimethylpenam-3-carboxylate 1,1-dioxide The title compound (708 mg, 69%) was obtained from allyl 6β-[(allyloxycarbonyl)acetamido] -2,2-dimethylpenam-3-carboxylate 1,1-dioxide (829 mg, 2 mmol) as a yellow foam, using the procedure described for Example 2, method B: IR (CHCl$_3$) 1810, 1755, 1690 cm$^{-1}$; $^1$H NMR (CDCl$_3$) δ 1.39 and 1.60 (each 3H, s, C$_2$-(CH$_3$)$_2$), 3.34 (4H, s, SCH$_2$CH$_2$S), 4.51 (1H, s, C$_3$-H), 4.60–4.85 (5H, m, 2xOCH$_2$CH=CH$_2$ and C$_5$-H), 5.24–5.42 (4H, m, 2xOCH$_2$CH=CH$_2$), 5.85–6.08 (2H, m, 2xOCH$_2$CH=CH$_2$), 6.30 (1H, dd, J=5 and 10Hz, C$_6$-H), 9.47 (1H, d, J=10Hz, NH).

C. Disodium 6β-[carboxylato(1,3-dithiolan-2-ylidene)acetamido]-2,2-dimethylpenam-3 -carboxylate 1,1-Dioxide According to the procedure described above for Example 4, method C, the title compound (433 mg, 90%) was prepared from allyl 6β-[(allyloxycarbonyl)(1,3-dithiolan-2-ylidene)acetamido] -2,2-dimethylpenam-3-carboxylate 1,1-dioxide (517 mg, 1 mmol) as a light yellow powder: $^1$H NMR (D$_2$O) δ 1.30 and 1.45 (each 3H, s, C$_2$-(CH$_3$)$_2$), 3.18–3.30 (4H, m, SCH$_2$CH$_2$S), 4.21 (1H, s, C$_3$-H), 5.09 (1H, d, J=4Hz, C$_5$-H), 5.98 (1H, d, J=4Hz, C$_6$-H).

EXAMPLE 6

Preparation of 6β-[(Allyloxycarbonyl)(1,3-dithiolen-2-ylidene)acetamido]-2,2-dimethylpenam-3-carboxylic acid, the ally ester and its sodium salt A. (2-Bromo-1-chloroethyl)phenylsulfoxide To a cooled solution of thiophenol (5.50 g, 50 mmol) and 1,2-dibromoethane (37.6 g, 200 mmol) in 150 mL of dichloromethane at 0° C. was added triethylamine (5.05 g, 50 mmol) dropwise. After 2 h of stirring, the mixture was washed with water and saturated NaCl solution, dried over Na$_2$SO$_4$, and concentrated in vacuo.

The obtained residue was dissolved in 100 mL of dichloromethane, and treated with sulfuryl chloride (6.75 g, 50 mmol) at 0° C. The mixture was stirred at 0° C for 1 h, concentrated to dryness under vacuum. The residue was again dissolved in 200 mL of dichloromethane, cooled to 0° C. and treated with 3-chloroperoxybenzoic acid, 50% (20.71 g, 60 mmol). The mixture was stirred at the same temperature for 15 min, washed with a mixed aqueous solution of sodium bicarbonate and sodium thiosulfate, and then with saturated NaCl. The organic layer was dried over Na$_2$SO$_4$ and concentrated in vacuo to give the residue which was purified by silica gel column chromatography with chloroform-ethyl acetate (98:2) as an eluant to give the title sulfoxide (3.15 g, 24%) as a colorless oil: $^1$H NMR (CDCl$_3$) δ3.88–4.02 (2H, m, —CHCH$_2$Br), 4.60–4.66 (1H, m, CHCH$_2$Br) 7.55–7.85 (5H, m, aromatic H).

B. Allyl 6β-[(allyloxycarbonyl)(1,3-dithiolen-2-ylidene)acetamido]-2,2-dimethylpenam-3-carboxylate To a solution of allyl 6β-[(allyloxycarbonyl)acetamido]-2,2-dimethylpenam-3-carboxylate (3.20 g, 8.37 mmol) and carbon disulfide (3.2 g, 42 mmol) in sieve-dried dimethylformamide 10 mL was added sodium hydride, 60% (0.669g, 16.7 mmol) portionwise at 0° C. The mixture was stirred for 15 min, then was added (2-bromo-1-chloroethyl)phenylsulfoxide (2.67 g, 10 mmol). The reaction mixture was stirred at room temperature for 30 min, poured into ice-water, extracted with benzene-ethyl acetate (1:1) mixture. The organic layer was washed several times with water, washed with saturated NaCl solution, dried over Na$_2$SO$_4$ and concentrated to give the residue which was used for the next reaction without further purification.

The crude dithiolane derivative obtained above was dissolved in 20 mL of toluene and the mixture was heated to reflux for 15 min. The solution was concentrated, and the resulting residue was purified by silica gel column chromatography with chloroform-ethyl acetate (95:5) as an eluent to give the title compound (1.59 g, 39.4%) as a brown oil: $^1$H NMR (CDCl$_3$) δ 1.52 and 1.68 (each 3H, s, C$_2$-(CH$_3$)$_2$, 4.50 (1H, s, C$_3$-H), 4.55–4.90 (4H, m, 2xOCH$_2$CH=CH$_2$), 5.25–5.50 (5H, m, 2xOCH$_2$CH=CH$_2$ and C$_5$-H), 5.62 (1H, d, J=4Hz, C$_5$-H), 5.90 (1H, dd, J=4 and 9Hz, C$_6$-H), 5.60–6.10 (2H, m, OCH$_2$CH=CH$_2$), 7.26 (2H, s, SCH=CHS), 9.14 (1H, d, J=9Hz, NH).

C. Sodium 6β-[(allyloxycarbonyl)(1,3-dithiolen-2-ylidene)acetamido]-2,2-dimethylpenam-3-carboxylate Using the process described in Example 1, method C, the title compound (682 mg, 85% was obtained from allyl 6β-[(allyloxycarbonyl)(1,3-dithiolen-2-ylidene)acetamido]-2,2-dimethylpenam -3-carboxylate (965 mg, 2 mmol) as a light yellow powder: $^1$H NMR (CDCl$_3$) δ1.53 and 1.65 (each 3H, s, C$_2$-(CH$_3$)$_2$, 4.70–4.82 (3H, s, OCH$_2$CH=CH$_2$ and C$_3$-H), 5.33–5.50 (2H, m, OCH$_2$CH=CH$_2$), 5.73 (2H, s, C$_5$-H and C$_6$-H), 5.90–6.15 (1H, m, OCH$_2$CH=CH$_2$), 7.21 (2H, s, SCH=CHS).

We claim:

1. A 6β-substituted penicillanic acid of the formula XII:

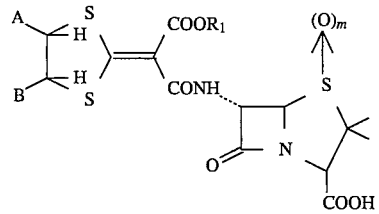

or a pharmaceutically acceptable salt or ester thereof, wherein

A and B are each hydrogen wherein the carbon atoms to which A and B are attached are linked by a single bond, or A and B together form a bond, wherein the carbon atoms to which A and B are attached are linked by a double bond, R1 is selected from the group consisting of a) hydrogen, b) a pharmaceutically acceptable salt and c) a pharmaceutically acceptable group selected from the group consisting of methyl; ethyl; propyl; isopropyl; propenyl; propynyl; butyl; isobutyl; tert-butyl; butenyl; butynyl; pentyl; pentenyl; pentynyl; hexyl; heptyl; octyl; nonyl; decyl; cyclopropyl; cyclobutyl; cyclopentyl; cyclopentenyl; cyclohexyl; cyclohexenyl; cycloheptyl; cyclooctyl; cyclononyl; cyclodecyl; allyl; phenyl; naphthyl; aralkyl, aralkenyl, and aralkynyl, wherein the aryl parts of the molecule are phenyl or naphthyl; heterocyclyl, heterocyclylalkyl, heterocyclylalkenyl, heterocyclylalkynyl and alkylheterocyclyl, wherein the heterocyclyl parts of the molecule consist of 1–5 carbon atoms and at least one hetero atom selected from the group consisting of nitrogen, oxygen and sulfur; wherein said group is unsubstituted or substituted with a substituent selected from the group consisting of floro; chloro; bromo; iodo; azido; nitro; monoalkyl substituted amino, dialkyl substituted amino, aryl substituted amino, alkanoylamino, arylcarbonylamino, cyano, hydroxy, alkoxy, aryloxy, alkanoyloxy, arylcarbonyloxy, mercapto, alkylthio, arylthio, alkanoylthio, arylcarbonylthio, oxyimino, alkoxyimino and carboxy, wherein the alkyl parts of the molecule contain 1 to 10 carbon atoms, the alkanoyl parts of the molecule contain 1 to 6 carbon atoms, and the aryl parts of the molecule are phenyl or naphthyl; and n is an integer between 0 and 2.

2. The compound according to claim 1, wherein said heterocyclyl is selected from the group consisting of pyridinyl, prazinyl, furyl, thienyl, imidazolyl, triazolyl, tetrazolyl, thiazolyl and oxazolyl.

3. The compound according to claim 1 wherein R1 is methyl.

4. The compound according to claim 1 wherein R1 is ethyl.

5. The compound according to claim 1 wherein R1 is hydrogen.

6. The compound according to claim 1, wherein the pharmaceutically acceptable salt is selected from the group consisting of alkali metal salts, alkaline earth metal salts, inorganic amine salts and organic amine salts.

7. The compound according to claim 1, wherein said compound is 6β-[(1,3-Dithiolan-2-ylidene)(methoxyycarbonyl)acetamido]-2,2-dimethylpenam-3-carboxylic acid.

8. The compound according to claim 1, wherein said compound is 6β-[(1,3-Dithiolan-2-ylidene)(ethoxycarbonyl)acetamido]-2,2-dimethylpenam-3-carboxylic acid.

9. The compound according to claim 1, wherein said compound is 6β-[(1,3-Dithiolan-2-ylidene)(ethoxycarbonyl)acetamido]-2,2-dimethylpenam-3-carboxylic acid 1,1-dioxide.

10. The compound according to claim 1, wherein said compound is 6β-[(1,3-Dithiolan-2-ylidene)(carboxy)acetamido]-2,2-dimethylpenam-3-carboxylic acid.

11. The compound according to claim 1, wherein said compound is 6β-[(1,3-Dithiolan-2-ylidene)(carboxy)acetamido]-2,2-dimethylpenam-3-carboxylic acid 1,1-dioxide.

12. The compound according to claim 1 wherein R1 is allyl.

13. The compound according to claim 1, wherein said compound is 6β-[(Allyloxycarbonyl)(1,3-dithiolen-2-ylidene)acetamido]-2,2-dimethylpenam-3-carboxylic acid.

14. A composition comprising a pharmaceutically effective amount of a compound according to claim 1 and a pharmaceutically acceptable carrier.

15. A pharmaceutical composition comprising
a) an amount of a compound according to claim 1 effective for protecting β-lactamase-susceptible β-lactam antibiotics from degradation by β-lactamases,
b) an amount of a β-lactam antibiotic effective for treating a bacterial infection, and
c) a pharmaceutically acceptable carrier.

16. The pharmaceutical composition according to claim 15, wherein said β-lactam antibiotic is selected from the group consisting of penicillin G, penicillin V, ampicillin, amoxicillin, carbenicillin, sulbenicillin, ticarcillin, azlocillin, mezlocillin, piperacillin, aztreonam, carumonam, imipenem, meropenem, biapenem, cephalothin, cephapirin, cephalexin, cephradine, cefroxime, cefaclor, cefadroxil, cefamandole, cefazolin, cefixime, cefmetazole, cefonicid, cefoperazone, cefotaxime, cefotetane, cefoxitin, ceftizoxime, ceftriaxon, ceftazidime, cefpirome and cefepime.

17. The composition according to claim 15, wherein the ratio of β-lactamase inhibitor and β-lactam antibiotic is between 1:10 and 10:1.

18. A method for treating bacterial infections caused by β-lactamase-producing bacteria comprising administering to a patient in need of such treatment, an amount of a β-lactam antibiotic effective for treating said bacterial infection in combination with an amount of a 6β-substituted penicillanic acid of the formula XII:

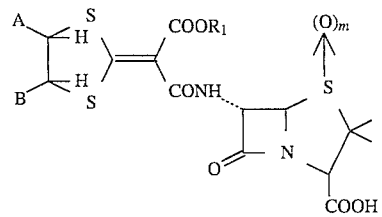

effective for protecting said β-lactam antibiotic from hydrolysis by β-lactamases,
wherein A and B are each hydrogen wherein the carbon atoms to which A and B are attached are linked by a single bond, or A and B together form a bond, wherein the carbon atoms to which A and B are attached are linked by a double bond, R1 is selected from the group consisting of a) hydrogen, b) a pharmaceutically acceptable salt and c) a pharmaceutically acceptable group selected from the group consisting of methyl; ethyl; propyl; isopropyl; propenyl; propynyl; butyl; isobutyl; tert-butyl; butenyl; butynyl; pentyl; pentenyl; pentynyl; hexyl; heptyl; octyl; nonyl; decyl; cyclopropyl; cyclobutyl; cyclopentyl; cyclopentenyl; cyclohexyl; cyclohexenyl; cycloheptyl; cyclooctyl; cyclononyl; cyclodecyl; allyl; phenyl; naphthyl; aralkyl, aralkenyl, and aralkynyl, wherein the aryl parts of the molecule are phenyl or naphthyl; heterocyclyl, heterocyclylalkyl, heterocyclylalkenyl, heterocyclylalkynyl and alkylheterocyclyl, wherein the heterocyclyl parts of the molecule consist of 1–5 carbon atoms and at least one hetero atom selected from the group consisting of nitrogen, oxygen and sulfur; wherein said group is unsubstituted or substituted with a substituent selected from the group consisting of floro; chloro; bromo; iodo; azido; nitro; monoalkyl substituted amino, dialkyl substituted amino, aryl substituted amino, alkanoylamino, arylcarbonylamino, cyano, hydroxy, alkoxy, aryloxy, alkanoyloxy, arylcarbonyloxy, mercapto, alkylthio, arylthio, alkanoylthio, arylcarbonylthio, oxyimino, alkoxyimino and carboxy, wherein the alkyl parts of the molecule contain 1 to 10 carbon atoms, the alkanoyl parts of the molecule contain 1 to 6 carbon atoms, and the aryl parts of the molecule are phenyl or naphthyl; and n is an integer of 0 to 2.

19. The method according to claim 18, wherein said β-lactam antibiotic is selected from the group consisting of penicillin G, penicillin V, ampicillin, amoxicillin, carbenicillin, sulbenicillin, ticarcillin, azlocillin, mezlocillin, piperacillin, aztreonam, carumonam, imipenem, meropenem, biapenem, cephalothin, cephapirin, cephalerin, cephradine, cefroxime, cefaclor, cefadroxil, cefamandole, cefazolin, cefixime, cefmetazole, cefonicid, cefoperazone, cefotaxime, cefotetane, cefoxitin, ceftizoxime, ceftriaxon, ceftazidime, cefpirome and cefepime.

20. The method according to claim 18, wherein said β-lactam antibiotic and said 6β-substituted penicillanic acid are administered simultaneously.

21. The method according to claim 18, wherein said

β-lactam antibiotic and said 6β-substituted penicillanic acid are administered separately.

22. The method according to claim 18, wherein said β-lactam antibiotic and said 6β-substituted penicillanic acid are administered orally, topically or parenterally.

23. A method for protecting a β-lactamase susceptible β-lactam antibiotic from degradation by β-lactamases, comprising adding a 6-βsubstituted penicillanic acid of the formula XII:

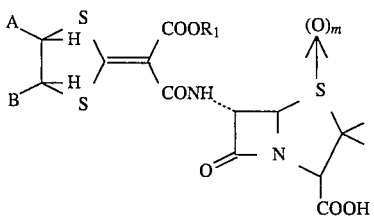

or a pharmaceutically acceptable salt or ester thereof to said β-lactam antibiotic,
wherein A and B are each hydrogen wherein the carbon atoms to which A and B are attached are linked by a single bond, or A and B together form a bond, wherein the carbon atoms to which A and B are attached are linked by a double bond, R1 is selected from the group consisting of a) hydrogen, b) a pharmaceutically acceptable salt and c) a pharmaceutically acceptable group selected from the group consisting of methyl; ethyl; propyl; isopropyl; propenyl; propynyl; butyl; isobutyl; tert-butyl; butenyl; butynyl; pentyl; pentenyl; pentynyl; hexyl; heptyl; octyl; nonyl; decyl; cyclopropyl; cyclobutyl; cyclopentyl; cyclopentenyl; cyclohexyl; cyclohexenyl; cycloheptyl; cyclooctyl; cyclononyl; cyclodecyl; allyl; phenyl; naphthyl; aralkyl, aralkenyl, and aralkynyl, wherein the aryl parts of the molecule are phenyl or naphthyl; heterocyclyl, heterocyclylalkyl, heterocyclylalkenyl, heterocyclylalkynyl and alkylheterocyclyl, wherein the heterocyclyl parts of the molecule consist of 1–5 carbon atoms and at least one hetero atom selected from the group consisting of nitrogen, oxygen and sulfur; wherein said group is unsubstituted or substituted with a substituent selected from the group consisting of floro; chloro; bromo; iodo; azido; nitro; monoalkyl substituted amino, dialkyl substituted amino, aryl substituted amino, alkanoylamino, arylcarbonylamino, cyano, hydroxy, alkoxy, aryloxy, alkanoyloxy, arylcarbonyloxy, mercapto, alkylthio, arylthio, alkanoylthio, arylcarbonylthio, oxyimino, alkoxyimino and carboxy, wherein the alkyl parts of the molecule contain 1 to 10 carbon atoms, the alkanoyl parts of the molecule contain 1 to 6 carbon atoms, and the aryl parts of the molecule are phenyl or naphthyl; and n is an integer of 0 to 2.

24. A pharmaceutical kit comprising the following components:
   a) the 6β-substituted penicillanic acid according to claim 1 in combination with a pharmaceutically acceptable carrier, and
   b) a β-lactam antibiotic in combination with a pharmaceutically acceptable carrier,
wherein said 6β-substituted penicillanic acid and said β-lactam antibiotic are in separate containers.

25. The pharmaceutical kit according to claim 24, wherein said β-lactam antibiotic is selected from the group consisting of penicillin G, penicillin V, ampicillin, amoxicillin, carbenicillin, sulbenicillin, ticarcillin, azlocillin, mezlocillin, piperacillin, aztreonam, carumonam, imipenem, meropenem, biapenem, cephalothin, cephapirin, cephalexin, cephradine, cefroxime, cefaclor, cefadroxil, cefamandole, cefazolin, cefixime, cefmetazole, cefonicid, cefoperazone, cefotaxime, cefotetane, cefoxitin, ceftizoxime, ceftriaxon, ceftazidime, cefpirome and cefepime.

* * * * *